(12) United States Patent
Shiozaki et al.

(10) Patent No.: US 7,799,953 B2
(45) Date of Patent: Sep. 21, 2010

(54) METHOD FOR PRODUCING 3-METHYLTHIOPROPANAL

(75) Inventors: Tetsuya Shiozaki, Saijo (JP); Toru Haga, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/665,006

(22) Filed: Sep. 22, 2003

(65) Prior Publication Data

US 2004/0063650 A1    Apr. 1, 2004

(30) Foreign Application Priority Data

Sep. 27, 2002    (JP) ............... 2002-282874

(51) Int. Cl.
*C07C 323/52* (2006.01)
*C07C 319/18* (2006.01)

(52) U.S. Cl. ....................................... 568/41

(58) Field of Classification Search .......... 568/41; 558/351, 438; 652/512; 658/438
See application file for complete search history.

(56) References Cited

U.S. PATENT DOCUMENTS 2,776,996 A  * 1/1957  Hunt et al. ................. 568/41
3,529,940 A    9/1970  Mitsuyoshi et al.
4,225,516 A  * 9/1980  Biola et al. ................. 568/41
5,352,837 A  * 10/1994 Hsu et al. ................... 568/41
5,386,056 A  * 1/1995  Matsuoka ................... 562/526
5,605,171 A  * 2/1997  Tam .......................... 136/253
5,637,766 A  * 6/1997  Hsu et al. ................... 562/512
5,663,409 A  * 9/1997  Blackburn et al. .......... 558/351
5,705,675 A  * 1/1998  Blackburn et al. .......... 558/351
5,744,647 A  * 4/1998  Hsu et al. ................... 568/41
5,925,794 A  * 7/1999  Hsu et al. ................... 568/41
6,031,138 A    2/2000  Hsu et al.

FOREIGN PATENT DOCUMENTS

GB       1166961       * 10/1969

* cited by examiner

*Primary Examiner*—Peter G O'Sullivan
(74) *Attorney, Agent, or Firm*—Sughrue Mion, PLLC

(57) ABSTRACT

A 3-methylthiopropanal is produced by a method comprising the step of supplying an acrolein and a methyl mercaptan together or sequentially with an acidic compound and a basic compound into a reaction system to react the acrolein with the methyl mercaptan, wherein the basic compound is used in an amount of about 0.3 mol or less per mol of the acidic compound. In accordance with the present invention, a 3-methylthiopropanal with high quality is produced while suppressing the production of by-products having high boiling points.

5 Claims, No Drawings

METHOD FOR PRODUCING 3-METHYLTHIOPROPANAL

BACKGROUND OF THE INVENTION

1. Field of the Invention

The present invention relates to a method for producing a 3-methylthiopropanal by reacting an acrolein with a methyl mercaptan. 3-Methylthiopropanal is useful as an intermediate for producing a methionine as a feed supplement, a hydroxy analogue thereof (e.g., 2-hydroxy-4-methylthiobutanoic acid) and the like.

2. Description of the Background Art

Conventionally, a method of reacting an acrolein and a methyl mercaptan using an acid/base mixed catalyst is known as one of methods for producing a 3-methylthiopropanal. For example, U.S. Pat. No. 2,776,996 describes a method of supplying an acrolein and an acid into a mixture which has been prepared by mixing a methyl mercaptan and a base at a molar ratio of acid/base of 0.05 to 10. GB Patent No. 1,166,961 describes a method of supplying a methyl mercaptan into a mixture of an acrolein, an acid and a base, and a method of co-supplying an acrolein, a methyl mercaptan, an acid and a base. In both methods of the GB Patent, the base is used in excess amount than that of the acid. Further, U.S. Pat. No. 6,031,138 describes a method of co-supplying an acrolein, a methyl mercaptan, an acid and a base while using the base in equimolar amount to that of the acid.

However, these method have problems such that by-products having high boiling points tend to be produced and the resulting 3-methylthiopropanals do not necessarily get satisfactory quality.

SUMMARY OF THE INVENTION

One of objects of the present invention is to provide a method for producing a 3-methylthiopropanal with a high quality under suppressing the production of by-products having high boiling point.

The present inventors have intensively studied, and resultantly have found that when an acrolein, a methyl mercaptan, an acidic compound and a basic compound are mixed by controlling the amount ratio of the basic compound to that of the acidic compound, the production of by-products with high boiling point, such as a 3-hydroxy-2-methylthiomethyl-4-pentenal and a 2-methylthiomethyl-5-methylthio-2-pentenal, can be suppressed to attain the above-mentioned object. The present invention has been accomplished based on such a finding.

Namely, the present invention provides a method for producing a 3-methylthiopropanal, the method comprising the step of supplying an acrolein and a methyl mercaptan together or sequentially with an acidic compound and a basic compound into a reaction system to react the acrolein with the methyl mercaptan, wherein the basic compound is used in an amount of about 0.3 mol or less per mol of the acidic compound.

DETAILED DESCRIPTION OF THE INVENTION

In the present invention, an acrolein, a methyl mercaptan, an acidic compound and a basic compound are supplied into a reaction system (such as a reactor) so that the acrolein and the methyl mercaptan are reacted with each other to obtain a reaction mixture containing a 3-methylthiopropanal. The acrolein and the methyl mercaptan may be supplied together or sequentially with the acidic compound and the basic compound. For example, the acrolein, the methyl mercaptan, the acidic compound and the basic compound are supplied separately but nearly at the same time into the reaction system. Alternatively, as mentioned below, the acrolein, the methyl mercaptan and a mixture of the acidic compound with the basic compound can be supplied separately but at the same time into the reaction system. Further, the acrolein and the methyl mercaptan may be supplied into the acidic compound, into which the basic compound is then added. The acrolein and the methyl mercaptan may be supplied into the basic compound, into which the acidic compound is then added. The above raw materials may be supplying into the reaction system intermittently.

The reaction can be carried out in a continuous manner such that the above-mentioned raw materials are supplied into the reaction system while taking the resulting reaction mixture out of the reactor system.

The methyl mercaptan may be used in about the same molar amount as that of the acrolein. From the standpoint of suppressing the odor of the resulting 3-methylthiopropanal, it is preferred that the acrolein is used in an amount slightly larger than the methyl mercaptan. For example, the methyl mercaptan is preferably used in an amount of 0.95 to 0.99 mol per mol of acrolein.

The acidic compound used in the present invention may be any of inorganic acids and organic acids. Examples of the inorganic acid include an oxo acid such as a sulfuric acid and a phosphoric acid; and a hydrogen halide such as a hydrogen fluoride, a hydrogen chloride and a hydrogen bromide. Examples of the organic acid include an aliphatic monocarboxylic acid such as a formic acid, an acetic acid, a propionic acid, an octanoic acid, an acrylic acid, a trichloroacetic acid and a trifluoroacetic acid; an aliphatic polycarboxylic acid such as an oxalic acid, a succinic acid and an adipic acid; an aromatic monocarboxylic acid such as a phenylacetic acid, a benzoic acid, a cinnamic acid, a furoic acid and a thiophenecarboxylic acid; and an aromatic polycarboxylic acid such as a phthalic acid; a sulfuric acid monoester; and a sulfonic acid. Among them, a carboxylic acid is preferred.

Examples of the basic compound include an inorganic base such as an ammonia, a sodium hydroxide, a potassium hydroxide, an ammonium carbonate, a sodium carbonate, a potassium carbonate, a sodium hydrogen carbonate, a potassium hydrogen carbonate, an ammonium acetate, a sodium acetate and a potassium acetate; and a nitrogen-containing organic base such as a piperidine, a triethylamine, a triethanolamine, a pyridine, a quinoline, an urotropin and an N,N-dimethylaniline.

In the present invention, a basic compound is used in an amount of about of 0.3 mol or less per mol of an acidic compound. By thus controlling the amount ratio of the basic compound to the acidic compound, the production of by-products with high boiling point, such as a 3-hydroxy-2-methylthiomethyl-4-pentenal and a 2-methylthiomethyl-5-methylthio-2-pentenal, can be suppressed to produce a 3-methylthiopropanal with high quality. The basic compound may be used in an amount of at least about 0.05 mol per mol of the acidic compound. Preferably, the basic compound is used in an amount of from about 0.1 molar to about 0.25 mol per mol of the acidic compound.

The acidic compound may be used in an amount of from about 0.001 mol to 0.05 mol, and preferably is used in an amount of from about 0.005 mol to about 0.02 mol, per mol of methyl mercaptan.

The acidic compound and the basic compound can be supplied separately or together with each other into the reaction system. From the standpoint of operationality and the like, it is preferred that both of them are previously mixed with each other to provide a mixture thereof, which is used as a supplying raw material stock. Further, in the present invention, components other than the above-described raw materials, such as a solvent inert to the reaction, may be used if necessary.

The reaction may be conducted at a temperature of from about 40° C. to about 100° C., and is preferably conducted at a temperature of from about 60° C. to about 80° C. for a period of time of, for example, from 10 minutes to 24 hours. The reaction may be conduced under any of reduced pressure, normal pressure and increased pressure.

The post treatment of the resulting reaction mixture containing a 3-methylthiopropanal can be appropriately selected from known methods. For example, the reaction mixture may be distilled so as to separate and/or purify a 3-methylthiopropanal from the mixture.

In accordance with the present invention, a 3-methylthiopropanal with high quality can be produced from an acrolein and a methyl mercaptan while suppressing the production of by-products with high boiling points.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2002-282874 filed on Sep. 27, 2002 indicating specification, claims and summary are incorporated herein by reference in their entirety.

EXAMPLES

The present invention is described in more detail by following Examples, which should not be construed as a limitation upon the scope of the present invention.

Example 1

Into a loop-type reactor which has an acrolein feeding port, a methyl mercaptan feeding port, an acetic acid/pyridine mixture feeding port and a reaction mixture outlet port connected to a residence tank, 100 parts by weight of an acrolein having a purity of 92% by weight, 77.9 parts by weight of a methyl mercaptan and 0.98 parts by weight of a mixture of an acetic acid and a pyridine having a molar ratio of acetic acid/pyridine of 1/0.13 were fed per unit period of time, to conduct a continuous reaction at a temperature of 70° C. with a residence time of 45 to 50 minutes. During this operation, the resulting reaction mixture was circulated in the loop-type reactor at a rate of 2500 parts by weight per unit period of time.

The reaction mixture was analyzed with a high performance liquid chromatography to obtain area percentage values of components in the mixture. As a result, the percentages of unreacted raw materials, i.e., acrolein and methyl mercaptan, are 0.049% and 0.004%, respectively; the percentage of 3-methylthiopropanal is 88.25%; and the percentages of by-products with high boiling point, 3-hydroxy-2-methylthiomethyl-4-pentenal and 2-methylthiomethyl-5-methylthio-2-pentenal, are 0.24% and 0.06%, respectively.

Example 2

The same operation was conducted as in Example 1 except that 1.03 parts by weight of a mixture of acetic acid and pyridine with a molar ratio of acetic acid/pyridine of 1/0.15 was fed instead of using 0.98 parts by weight of the mixture of acetic and pyridine with a molar ratio of acetic acid/pyridine of 1/0.13.

The resulting reaction mixture was analyzed with a high performance liquid chromatography to obtain area percentage values of components in the mixture. As a result, the percentages of unreacted raw materials, i.e., acrolein and methyl mercaptan, are 0.034% and 0.011%, respectively; the percentage of 3-methylthiopropanal is 88.01%; and the percentages of by-products with high boiling points, 3-hydroxy-2-methylthiomethyl-4-pentenal and 2-methylthiomethyl-5-methylthio-2-pentenal, are 0.23% and 0.06%, respectively.

Comparative Example 1

The same operation was conducted as in Example 1 except that 0.73 parts by weight of a mixture of acetic acid and pyridine with a molar ratio of acetic acid/pyridine of 1/0.51 was fed instead of using 0.98 parts by weight of the mixture of acetic acid and pyridine with a molar ratio of acetic acid/pyridine of 1/0.13.

The resulting reaction mixture was analyzed with a high performance liquid chromatography to obtain area percentage values of components in the mixture. As a result, the percentages of unreacted raw materials, i.e., acrolein and methyl mercaptan, are 0.02% and 0.15%, respectively; the percentage of 3-methylthiopropanal is 89.26%; and the percentages of by-products of high boiling point, 3-hydroxy-2-methylthiomethyl-4-pentenal and 2-methylthiomethyl-5-methylthio-2-pentenal are 0.73% and 0.10%, respectively.

Comparative Example 2

The same operation was conducted as in Example 1 except that 1.45 parts by weight of a mixture of acetic acid and pyridine with a molar ratio of acetic acid/pyridine of 1/0.51 was fed instead of using 0.98 parts by weight of the mixture of acetic acid and pyridine with a molar ratio of acetic acid/pyridine of 1/0.13.

The resulting reaction mixture was analyzed by a high performance liquid chromatography to obtain area percentage values of components in the mixture. As a result, the percentages of unreacted raw materials, i.e., acrolein and methyl mercaptan, are 0.212% and 0.02%, respectively; the percentage of 3-methylthiopropanal is 87.79%; and the percentages of by-products of high boiling point, 3-hydroxy-2-methylthiomethyl-4-pentenal and 2-methylthiomethyl-5-methylthio-2-pentenal are 0.41% and 0.12%, respectively.

What is claimed is:

1. A method for producing a 3-methylthiopropanal in a continuous manner, the method comprising the step of supplying an acrolein and a methyl mercaptan together or sequentially with an acidic compound and a basic compound into a reaction system to react the acrolein with the methyl mercaptan, wherein the basic compound is used in an amount of 0.3 mol or less per mol of the acidic compound, and wherein the acidic compound is an aliphatic carboxylic acid and the basic compound is a nitrogen-containing organic base.

2. The method according to claim 1, wherein the acrolein and the methyl mercaptan are supplied together with the acidic compound and the basic compound into the reaction system.

3. The method according to claim 2, wherein the acidic compound and basic compound are previously mixed with each other before being supplied into the reaction system.

4. The method according to any one of claims 1 to 3, wherein the basic compound is used in an amount of from 0.05 to 0.3 mol, per mol of the acidic compound.

5. The method according to claim 4, wherein the basic compound is used in an amount of from 0.1 to 0.25 mol, per mol of the acidic compound.

* * * * *